United States Patent [19]

Miller

[11] 4,338,925

[45] Jul. 13, 1982

[54] PRESSURE INJECTION OF BONE CEMENT APPARATUS AND METHOD

[76] Inventor: Jo Miller, 641 Argyle Ave., Westmount, Quebec, Canada

[21] Appl. No.: 105,573

[22] Filed: Dec. 20, 1979

[51] Int. Cl.³ .................... A61F 5/04; A61M 3/00; A61M 35/00

[52] U.S. Cl. .................... 128/92 E; 128/245; 128/261

[58] Field of Search ............. 128/218 R, 218 D, 215, 128/234, 236, 242, 239, 245, 261, 92 R, 92 E, 207.23, 207.24, 207.25

[56] References Cited

U.S. PATENT DOCUMENTS

| | | | |
|---|---|---|---|
| 546,073 | 9/1895 | Mix | 81/15.6 |
| 2,732,102 | 11/1951 | Ekins | 222/327 |
| 2,750,943 | 6/1956 | Dann | 128/218 D |
| 2,778,541 | 1/1957 | Sherbondy | 222/327 |
| 3,058,632 | 5/1957 | Stremmel | 222/567 |
| 3,112,743 | 9/1960 | Cochran et al. | 128/92 |
| 3,141,583 | 7/1964 | Mapel et al. | 128/218 D |
| 3,160,156 | 12/1964 | Tyler | 128/218 R |
| 3,193,146 | 10/1962 | Isgriggs et al. | 222/82 |
| 3,255,747 | 9/1960 | Cochran et al. | 128/92 |
| 3,422,814 | 1/1969 | Lloyd | 128/245 |
| 3,721,229 | 3/1973 | Panzer | 128/245 |
| 3,765,413 | 10/1973 | Lepar | 128/245 |
| 3,894,663 | 7/1975 | Carhart et al. | 222/309 |
| 4,090,639 | 5/1978 | Campbell et al. | 222/43 |
| 4,274,163 | 6/1981 | Malcom et al. | 128/92 C |

OTHER PUBLICATIONS

Zimmer brochure "The Miller TM Cement Delivery System" (A flyer showing the instant device).
A. J. C. Lee et al. "A device to improve the extrusion of bone cement into the bone of the acetabulum in the replacement of the hip joint", Biomed. Eng. 9 (11): 522-4 (Nov. 1974).
T. Sloof, "The Influence of Acrylic Cement on the Fixation of Hip Prostheses", pp. 23-25.
"Improve the strength of the cement and of the cement/bone interface with the instruments comprising the Exeter Cement Security System", *Howmedica International, Inc.* 1977.
"The Jet Vac System: A Method That Helps Preserve Bone Cement Strength", Richards, J. of Bone & Joint Surgery, 59A No. 8, Dec. 1977.
"Lidge Cement Gun", DePuy–Division of Bio Dynamics, Inc. P.O. Box 988 Warsaw, Ind. 46580.
Hallel, T., et al., "Polymethylmethacrylate in the Knee" *JBJS*, vol. 58-A, No. 4, Jun. 1976, pp. 556-557.
"The Hand Injector" Cordis Corp. P.O. Box 370428 Miami, Fla. 33137 Apr. 1978.
"Packaging and Application Systems for Single and Multi-Component Materials" SEMCO P.O. Box 1800 San Fernando Road, Glendale, CA 91209.

*Primary Examiner*—Stephen C. Pellegrino
*Assistant Examiner*—C. W. Shedd
*Attorney, Agent, or Firm*—Sherman & Shalloway

[57] ABSTRACT

A penetrating bone cement, for example a cement having a viscosity at 68° to 70° F. of less than 5000 poise and, preferably, less than 2000 poise up to the fifth or sixth minute after the cement is mixed, is injected under high pressure such that the bone cement penetrates the trabeculae of the bone to provide an improved fixation interface between the bone cement and bone. The bone cement is placed within a reinforced, front loading cartridge having a plunger at one end thereof and a nozzle at the other end thereof.

The end of the cartridge having the plunger engages a high pressure injection gun including a housing axially supporting a rod with respect to the cartridge. Carried on the rod is a forward engaging member cooperating with a lever pivoted to the housing. Manual rotation of the lever engages the forward engaging member and forces the rod forward to force the plunger into the cartridge. A single manual actuation of the lever results in the extrusion of approximately two cubic cm of bone cement from the cartridge and through the nozzle. In the preferred embodiment, one end of the cartridge is flanged and engages the housing by means of a bezel. The lever is in the form of a trigger pivotally connected to the handle and having a notch engaging the forward engaging member. A rearward engaging member is also provided to prevent rearward movement of the rod and a release pin releasably engages the rearward engaging member. The front of the cartridge includes a front closure cap which contains the cement in the front-loading cartridge and which is configured to receive a plurality of different shaped tips.

7 Claims, 6 Drawing Figures

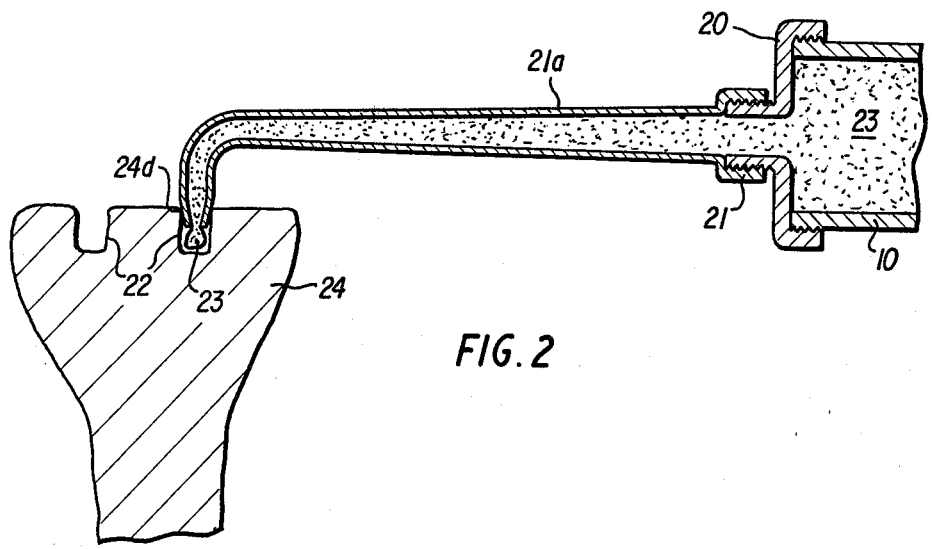
FIG. 2
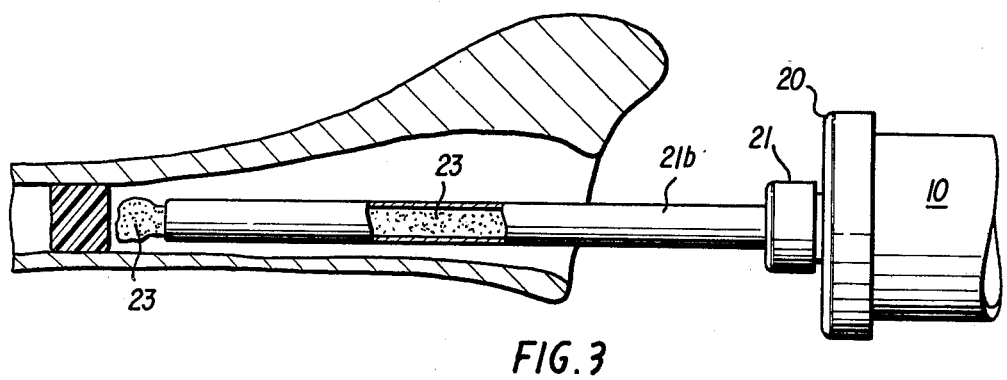
FIG. 3
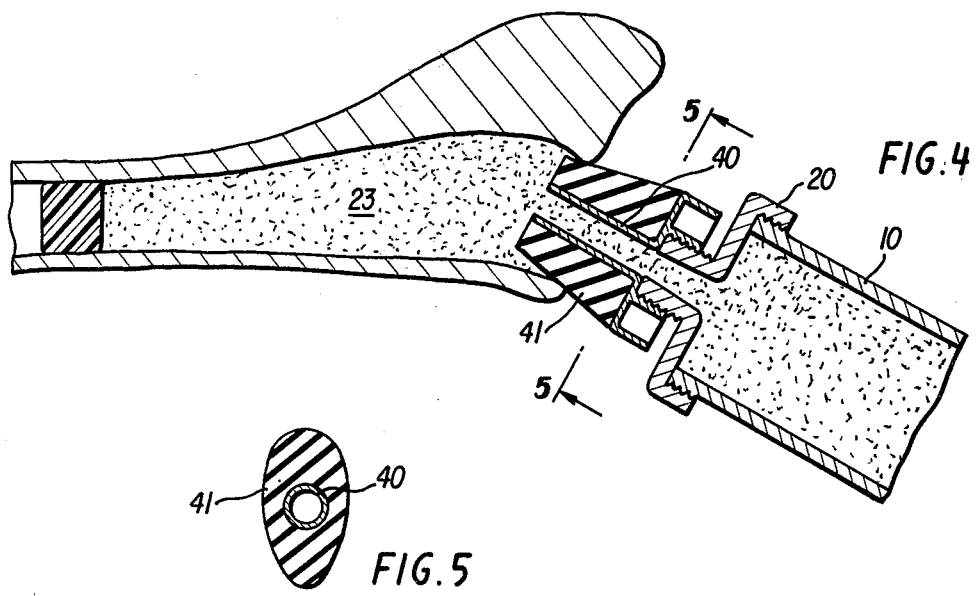
FIG. 4
FIG. 5

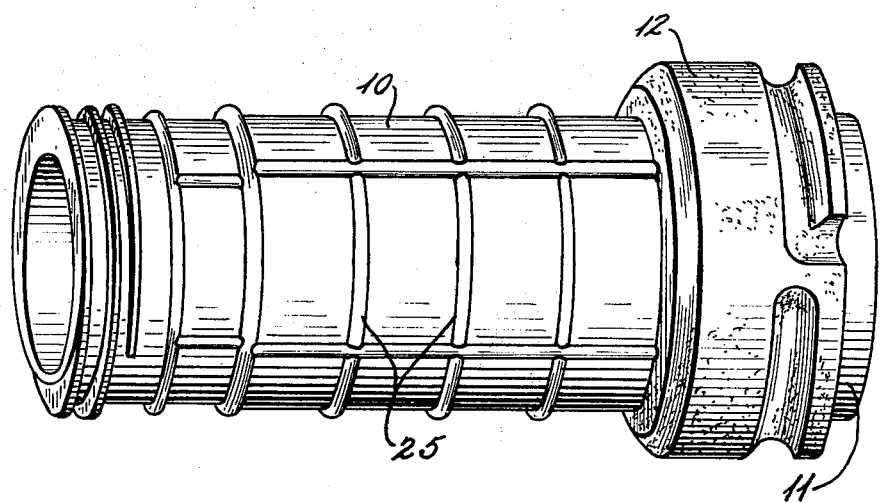

PRESSURE INJECTION OF BONE CEMENT APPARATUS AND METHOD

BACKGROUND OF THE INVENTION

1. Field of the Invention

The invention generally relates to improved fixation of a prosthetic component to bone and, in particular, relates to an apparatus for and method of pressure injection of low viscosity bone cement into bone surfaces to improve the bone/cement interface.

2. Description of the Prior Art

Total arthroplasty has become widely accepted as a useful measure in the treatment of severe arthritis. It facilitates the correction of deformity, the reestablishment of stability and, most important, the relief of pain. Unfortunately, the procedure is associated with a number of complications including loosening of the arthroplasty components. A number of factors contribute to loosening including failure to correct a deformity, an overweight or overactive patient, an osteoarthritic joint in comparison to a rheumatoidal joint and the use of a constrained prosthesis. The consequences of loosening include return of pain and deformity, the need for further reconstructive surgery with attendant technical difficulties and increased risk of sepsis and the possible risk of subsequent re-loosening. Failure of the fixation may originate at the interface between the prosthesis and cement, at the interface between the cement and bone, or both.

Loosening of the joint arthroplasty components occurs in a number of ways. Resorption of the bone commonly occurs, particularly, around the stem of a constrained prosthesis and is the result of high loads placed on the cement/bone interface leading to micromovement, resorption and gross loosening. Separation of the cement from the bone is usually due to a weak bone/cement interface and results in gross displacement of the implant. A radiolucent line is commonly seen between the cement and bone and has the following characteristics. Microscopic examination of the interface between the cement and bone indicates that the radiolucent line corresponds to a fibrous membrane which has developed at the interface. Mechanically, the fibrous membrane presents a plane of weakness between the cement and bone and a potential site for loosening. Micromovement occurs at those interfaces where a fibrous membrane is interposed. The radiolucent line, therefore, represents a site of impaired mechanical integrity.

Failure of the cement/bone interface may be due to a mechanically incompetent interface from the moment of implantation. The doughy cement presently employed and having a viscosity at 68° to 70° F. of greater than 4000 poise at the 5th or 6th minute after mixing is applied to cancellous surfaces by hand and penetrates trabeculae in the bone only to a limited degree, if at all. More practically it may conform to surface irregularities, but does not penetrate the bone. Poor fixation of this type leads to micromovement which in turn leads to bone resorption which results in the development of a fibrous membrane. Acrylic cements as currently used for the fixation of joint arthroplasty components to bone has inherent deficiencies in terms of establishing secure and enduring interfaces between the prosthesis and the cement and between the cement and the bone.

Guns which are presently available for injecting cement generate a low pressure and are prone to blockage by the thickening cement. Therefore, the low pressure guns of the prior art are ineffectual in inducing cement to penetrate bone.

In addition, these guns are non-modular and are not suitable for a variety of tasks other than introducing cement into the upper end of the femur without pressurization.

SUMMARY OF THE INVENTION

It is an object of this invention to describe a cement injecting apparatus which employs high pressure and low volume output.

It is another object of this invention to describe a system for preparing a bone area for receiving a prosthetic component including a front-loading reinforced cartridge for receiving a penetrating bone cement.

It is another object of this invention to describe a cement delivery system employing a variety of tips allowing for a variety of special applications.

It is yet another object of this invention to describe a system for preparing a bone area for receiving a prosthetic component which is extremely powerful and effective in delivering high viscosity cement.

In order to overcome the above problems, a mechanically secure interface between the prosthesis, cement and bone can be accomplished by inducing the cement to form a microinterlock with the prosthesis surface and the bone. Pressure injection of acrylic cement into bone surfaces results in an improved fixation by microinterlock. Such pressure injection induces the cement to actually penetrate between the trabeculae of the bone, displacing the marrow and producing firm fixation at a multitude of sites. In order to accomplish bone penetration and interlock, the cement must be used in a workable state. A bone cement having a low viscosity during the working period has been found advantageous for achieving the bone-cement interlock according to the invention. The pressure injection of a low viscosity acrylic cement by an apparatus and method according to the invention results in an improved fixation by microinterlock. The cement actually penetrates between the trabeculae, displacing the marrow and producing firm fixation at a multitude of sites.

The system according to the invention is used for preparing bone surfaces for receiving a prosthetic component. A cartridge containing a penetrating bone cement is placed within an injection gun for extruding the bone cement from the cartridge. A nozzle and front closure cap fitted at the end of a front loading cartridge allow the pressure injection of the penetrating bone cement into the bone cavity or onto a cut bone surface. The purpose for a front loading cartridge is to allow for proper venting of entrapped air in the cartridge. Present rear-loading cartridges entrap air at the rear of the cartridge between the cement and the plunger. Since the entrapped air has no means of escape, it can become entrapped in the cement which could lead to failure of the cement. Also, such trapped air is compressible, so that energy which is intended to be delivered against the contents of the cartridge is wasted in compression of the trapped air. Subsequent release of pressure and re-expansion of the trapped air tends to extrude cement from the gun at times and locations at which cement delivery is not desired.

Furthermore, the modular system allows a variety of different tips of varying size to be attached to the cartridge for varying tasks or applications. For example, the nozzle may be sized to fit the circumference of bone cavity so that the cavity may be sealed and cement may be forcefully injected into the bone cavity. Alternatively, the nozzle may be designed to inject cement into fixation holes or into boney surfaces.

The injection gun according to the invention is of a high pressure type and includes a housing having an axial opening therein. The cartridge is placed within the axial opening of the housing and an internally-engaging collar is located within the axial opening to engage the flange of the cartridge and hold the cartridge in position. The end of the rod projecting from the housing includes a knob and the other end of the rod within the housing has a cap for engaging a plunger within the cartridge. The rod carries a forward engaging member which cooperates with a hinged trigger. The forward engaging member engages a notch on the trigger and rotational movement of the trigger forces the forward engaging member and, therefore, the rod forward. A coil spring is provided between the forward engaging member and a support in the housing so that the forward engaging member is returned to its initial position after forward movement of the rod. A rearward engaging member also engages the rod and prevents rearward movement of the rod. A release pin is associated with the rearward engaging member so that the rearward engaging member may be selectively released to withdraw the rod to a starting position.

BRIEF DESCRIPTION OF THE DRAWING

These features and objects of the invention will become apparent to those skilled in the art by referring to the accompanying drawing and following specification in which:

FIG. 2 is a sectional view of a tip according to the invention applying bone-cement to a bone cavity in a bone;

FIG. 3 is a view partially in section of a tip according to the invention depositing bone-cement into the femoral canal;

FIG. 4 is a sectional view of a tip according to the invention used to pressurize the bone cement in the femoral canal; and FIG. 5 is a sectional view taken along lines 5—5 of FIG. 4.

FIG. 6 depicts a front loading cartridge according to the invention having reinforcing ribs.

DETAILED DESCRIPTION OF THE INVENTION

Figure 1:
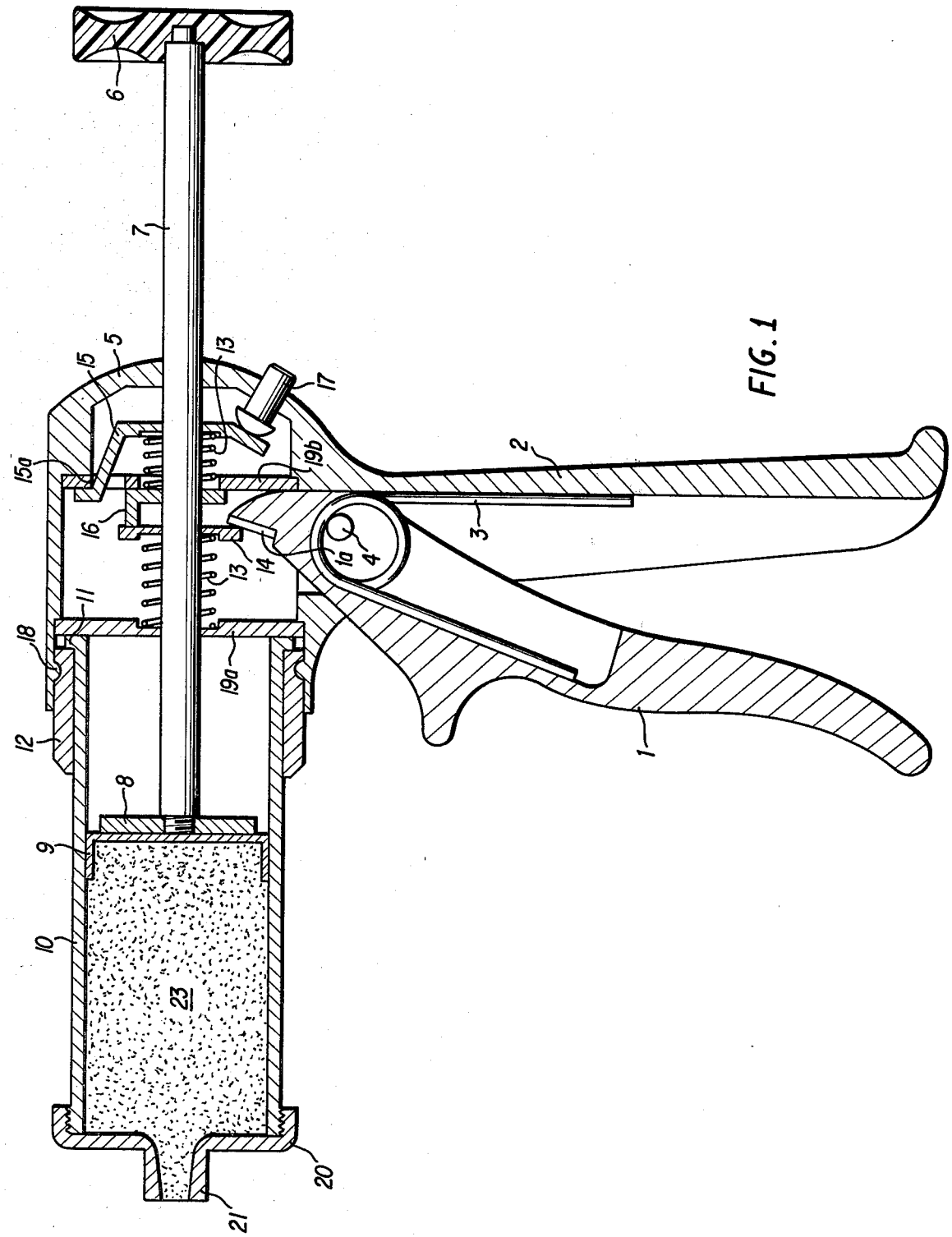
FIG. 1 is a sectional view of the injection gun and cartridge system according to the invention.

The cartridge means according to the invention contains a penetrating bone cement 23 held within a cylinder 10 having a flange 11 at one end thereof. The cartridge means includes a plunger 9 at one end thereof and a front closure cap at the opposite end allowing for front loading of the cement into the cartridge and which also allows for the interchangeability of tips. The cylinder wall 10 may be reinforced with ribs 25 for added strength.

As used herein, the term "penetrating bone cement" connotes a bone cement which is capable of penetrating the trabeculae of bones when applied thereagainst under substantial pressure during its period of workability. The best such penetrating cement presently known to me is an acrylic cement having a low viscosity of less than 2000 poise, at 68° to 70° F. during a working period of up to 5 or 6 minutes after mixing.

The means for extruding the preferred low viscosity bone-cement from the cartridge means includes a housing 5 with supports 19a and 19b and a handle 2 forming integral parts of the housing 5. The flange 11 of the cartridge means is located within an axial opening in the housing 5 and abuts the support 19a. A collar 12 internally engages the axial opening and bosses 18 project from the housing into the axial opening. Therefore, the flange 11 of the cartridge means is locked within the housing 5 between the support 19a and the collar 12.

Supports 19a and 19b have axial openings therein which are in registry and along the axis of the cylinder 10. These openings support rod 7 which is attached at one end thereof to a cap 8 for engaging the plunger 9 of the cartridge means. The other end of the rod 7 carries a knob 6. In order to move the rod, cap and plunger forward to extrude the bone cement 23 from the cartridge means, a forward engaging member 14 is provided on the rod between the supports 19a and 19b. The forward engaging member 14 is spaced away from the support 19a by coil spring 13. Trigger 1 is hinged to housing 5 by pivot pin 4 and carries a notch 1a which engages the forward engaging member.

A rearward engaging member 15 is also provided to hold the rod 7 in position and prevent unwanted rearward movement of the rod 7. The rearward engaging member 15 is hooked through an aperture 15a in the support 19b and has an axial opening through which the rod 7 is located. The rearward engaging member 15 is spaced away from the support 19b by coil spring 13. The end of the rearward engaging member 15 which is not hooked through aperture 15a is engaged by a release pin 17 slideably located within the housing 5.

The trigger 1 is shaped to allow grasping of the trigger 1 and handle 2 and the trigger 1 is biased in a counterclockwise position to be held open by a spring 3. It is contemplated that any convenient biasing means, such as resilient members, coil springs, etc. may be used to bias the trigger 1 away from the handle 2.

The front closure cap 20 and selected tip 21 form the means for applying the extruded low viscosity bone cement to the bone cavity and the means for pressurizing the low viscosity bone cement applied to the bone cavity.

In order to achieve effective pressurization of penetrating cement into the trabeculae of the bone, it is essential to have a cavity which can be closed off by the injector tip to create a closed space. A variety of tips are available for the various types of bone surfaces. There are basically two types of bone surfaces which need to be considered: (1) a plateau surface such as the tibial surface of the knee or the acetabular surface for the hip joint, and (2) a long tubular canal such as that in the long bone of the femur for a hip replacement.

When a prosthesis is to be cemented to a plateau-type surface, holes may be drilled into the bone surface to create a cavity into which bone cement is to be injected, as shown in FIG. 2. An appropriate tip is selected which is configured to interfit with the opening of the bone cavity. The end of the tip is tapered inwardly to terminate in a portion having a diameter less than the diameter of the bone cavity. This allows the tapered portion of the tip to be inserted into the bone cavity and form a seal about the diameter of the bone cavity. Thus, the cement is injected into a closed space so that pressure can build up to force the cement to penetrate the trabeculae of the bone. Cement is also deposited over the remaining bone surface to which the prosthesis is to be attached.

A tip 21a with a 90° bend as shown in FIG. 2 is used for a surface such as the tibia. A long straight tip is used for the acetabular surface. Both of these tips contain the tapered end.

In the case of a long tubular bone canal, some type of plug as shown in FIG. 3 must be lodged in the canal to create a closed space to prevent the extension of bone cement beyond the point where it is useful, and to facilitate more complete filling and pressurization of the canal. Various means of plugging the canal have been advocated, including plugs made of natural bone, polyethylene or a bolus of doughy bone cement.

Initially, a long straight tip 21b, which has a diameter less than the diameter of the canal to allow the tip to project into the bone canal, is used to deposit bone cement into the long bone canal. This tip 21b does not have a tapered end since the canal is initially just being filled up. Then a tip such as the femoral canal pressurizer 40 and adapter 41, as shown in FIG. 4, is used to complete the filling of the canal and pressurize the the contents of the cavity. The tapered pressurizer seals off the canal to enable the pressure created upon injection of the cement to force the cement to penetrate the bone.

Note in the above embodiments, the importance of sealing off a cavity to help pressurize the cement.

MODE OF OPERATION OF THE INVENTION

The system of fixation according to the invention begins with the mixing of penetrating bone cement and is followed by the location of the penetrating bone cement with the front loading cartridge 10. The front closure cap 20 is connected onto the cartridge 10. A tip 21 is selected for the particular type of operation and is engaged with the front closure cap 20. The engagement between the front closure cap 20 and the cartridge 10 may be by means of snap fit, an internal threading or an external threading. The flanged end 11 of the cylinder 10 is then closed off by locating plunger 9 within the cylinder 10. The flanged end is then placed within the axial opening of the housing 5 and collar 12 is slideably located over the cylinder 10 engaging the bosses 18 and affixing the flange 11 between the support 19a and the bezel 12.

At the same time the cartridge is engaged by the injection gun the rod 7 is placed in its rearmost position by pressing the release pin 17 and pulling rearwardly on the knob 6 until the cap 8 is against the support 19a. After the cartridge is engaged between the collar 12 and the support 19a, the knob 6 is pushed forward until the cap 8 engages the plunger 9. The injector gun with engaged cartridge is then positioned for the pressurized extrusion of the bone cement 23.

The surgeon performing the fixation grasps the handle 2 and trigger 1 and squeezes them together. This causes a counterclockwise rotation of the trigger 1 and about the pivot pin 4. Such rotation results in the notch 1a engaging the forward engaging member 14 at the lower portion thereof. This engagement locks the forward engaging member 14 onto the rod 7 and compresses the coil spring 13 thereby moving the rod 7, cap 8, plunger 9 and bone cement 23 located within the cylinder 10 in a forward direction and through the tip 21. The trigger 1 is then released and is returned to its original position by bias spring 3. Simultaneously, the coil spring 13 returns the forward engaging member 14 to its original position in engagement with notch 1a. A stop/release member 16 is provided so that the forward engaging member 14 returns to a position perpendicular to the rod 7. The forward engaging member 14 is held in perpendicular position so that the rod 7 may be moved forward merely by pushing on the knob 6 or it may be moved backward by releasing the rearward engaging member 15 via release pin 17. In order to reset the rod 7, pin 17 is pushed into the housing until the rearward engaging member 15 is perpendicular to the rod 7 and disengaged therefrom. The rod 7 can now be moved in either direction.

One critical feature of the invention is the ability of the injection gun to develop high pressure while applying a small amount of bone cement to the bone canal. In particular, the notch 1a, pivot pin 4 and trigger 1 are configured such that a single actuation of the trigger 1 results in sufficient forward movement of the forward engaging member 14 and rod 7 so that two or three cubic cm of bone cement 23 are ejected through the tip 21. In fact, the trigger 1 is configured according to the diameter of cylinder 10 so that the plunger 9 moves the equivalent to two or three mm linearly when the trigger 1 is squeezed and meets handle 2, which results in the extrusion of 2 to 3 cubic cm of cement. This feature of the invention is in contrast to guns of the prior art which were generally configured to eject 10 to 15 cubic cm at low pressure.

Various changes may be made in the details of the invention, as disclosed, without sacrificing the advantages thereof or departing from the scope of the appended claims. Furthermore, although the present invention has been disclosed and discussed with particular regard to its exceptional advantages in terms of a system for preparing a bone for receiving a prosthetic component, it may be understood that the invention may be employed in several surgical and industrial applications wherein a high pressure, low volume, low viscosity injection system is desired.

What is claimed is:

1. A system for injecting a low viscosity pre-mixed penetrating bone cement into a bone cavity, prior to placement of a prosthetic device into the bone cavity, under sufficient pressure to cause the cement to penetrate between the trabeculae of the bone, said system comprising;
   (a) cartridge means having an opening at one end thereof and a piston at the opposite end thereof, and a low viscosity bone penetrating cement having a viscosity, at 68° to 70° F., of less than 2,000 poises, up to about the sixth minute after the time of initial mixing of the cement, said opening functioning as both an inlet for loading said cement into said cartridge means and as an outlet from which said cement can be forced out of said cartridge means;
   (b) extruding means for forcing a low volume of about 2 to 3 cubic centimeters of the penetrating bone cement in said cartridge means to move towards said outlet opening, said extruding means comprising
      a housing for engaging the end of the cartridge having the piston;
      pressure means for forcing the piston into the cartridge means and comprising a rod supported in said housing in axial alignment with respect to said cartridge means, one end of said rod engaging the piston and a means for slideably engaging said rod; and manual activating means for actuating the pressure means and comprising a lever pivotally connected to the housing by a pivot pin, said lever having one end manually movable with respect to the housing and having the opposed end thereof engaging the means for slideably engaging the rod;

wherein said opposed end of the lever which engages the means for slideably engaging the rod, said pivot pin, and said lever are configured such that a single manual actuation of said lever causes said slideable engaging means to move said rod which moves said piston into the cartridge means a distance sufficient to forcibly eject said low volume of low viscosity penetrating bone cement through said outlet opening under substantial pressure sufficient to cause said cement to penetrate between the trabeculae of the bone; and (c) removable nozzle and pressure sealing means at the outlet opening of said cartridge means for applying the low volume of low viscosity penetrating bone cement forced from the cartridge means by the extruding means to the bone cavity and for providing a pressure seal between said bone cavity and said outlet opening, whereby said low volume of low viscosity penetrating bone cement will be injected into the bone cavity under said substantial pressure and will penetrate between the trabeculae of the bone to thereby provide a bone/cement interface to securely hold said prosthetic device in place, wherein said removable nozzle and pressure sealing means comprises a removable closure cap fitting over the outlet opening of said cartridge means and having an outlet orifice and at least one nozzle removably connectable to said outlet orifice, at least one of said nozzles having an outlet portion shaped to close against an entrance to a bone cavity to thereby provide said pressure seal between said bone cavity and said outlet opening.

2. The system of claim 1 wherein one of said at least one nozzle comprises an elongated tubular portion having an outlet tip which is tapered inwardly to terminate in a portion having a diameter less than the diameter of the bone cavity to be filled, said tapered portion of the tip forming the pressure seal between the bone cavity and the outlet opening.

3. The system of claim 1 or 2 wherein one of said at least one nozzle comprises a generally cylindrical tubular portion removably connectable to said outlet orifice of said closure cap and a generally inwardly tapered rubber portion fitting over the cylindrical tubular portion, said rubber portion being configured to fit within a femoral canal and provide a pressure seal between the femoral canal and the outlet opening.

4. The system of claim 1 further including first and second supports within said housing; each of said supports having an opening supporting the rod in axial alignment with respect to said cartridge means; said means for slideably engaging the rod comprising a first member located between said first and second supports, said first member having an opening therein, said rod passing through said opening; and biasing means pivotally biasing the lever in the housing in a direction in which the opposed end of said lever is biased in a direction away from said first member.

5. The system of claim 4 further including a second member supported by the housing and engaging the rod to prevent motion of the rod in the opposite direction from said outlet opening; and a release pin for selectively engaging the second member and disengaging the second member from the rod thereby allowing the rod to move in the direction away from the outlet opening.

6. The system of claim 5 wherein the end of the cartridge means having the piston is flanged and a collar is selectively connected to the housing and engages the flange.

7. The system of claim 6 wherein said cartridge means comprises a cartridge having reinforcing ribs.

* * * * *